United States Patent [19]

Rossmaier et al.

[11] Patent Number: 5,318,726

[45] Date of Patent: Jun. 7, 1994

[54] DERIVATIVE OF AMINOSUCCINIC ACID AS A COMPLEXING AGENT

[75] Inventors: Henry Rossmaier; Helmut Blum, both of Duesseldorf; Josef Steber, Langenfeld; Hans-Juergen Riebe, Hilden, all of Fed. Rep. of Germany

[73] Assignee: Henkel Kommanditgesellschaft auf Aktien, Duesseldorf, Fed. Rep. of Germany

[21] Appl. No.: 978,693

[22] PCT Filed: Jul. 24, 1991

[86] PCT No.: PCT/EP91/01382

§ 371 Date: Apr. 2, 1993

§ 102(e) Date: Apr. 2, 1993

[87] PCT Pub. No.: WO92/02489

PCT Pub. Date: Feb. 20, 1992

[30] Foreign Application Priority Data

Aug. 2, 1990 [DE] Fed. Rep. of Germany ....... 4024552

[51] Int. Cl.$^5$ ..................... C11D 3/33; C07C 227/14; C07C 229/24
[52] U.S. Cl. .............................. 252/546; 252/174.19; 252/174.23; 252/174.25; 252/548; 252/DIG. 11; 562/564; 562/565; 562/568; 562/571
[58] Field of Search .................. 252/174.19, 546, 527, 252/180, DIG. 11, 548, 529, 142; 562/564, 565, 567, 568, 571

[56] References Cited

U.S. PATENT DOCUMENTS

| | | | |
|---|---|---|---|
| 3,637,511 | 1/1972 | Yang | 252/527 |
| 3,929,874 | 12/1975 | Beermann et al. | 562/564 |
| 5,183,590 | 2/1993 | Carter et al. | 252/392 |

FOREIGN PATENT DOCUMENTS

| | | |
|---|---|---|
| 2241134 | 3/1974 | Fed. Rep. of Germany . |
| 3739610 | 6/1989 | Fed. Rep. of Germany . |
| 5170714 | 7/1993 | Japan . |
| 0629208 | 9/1978 | U.S.S.R. . |

OTHER PUBLICATIONS

Payne, G. B. and Williams, P. H., "Reactions of Hydrogen Peroxide, IV. Sodium Tungstate Catalyzed Epoxidation of $\alpha,\beta$-Unsaturated Acids", *J. Org. Chem.*, vol. 24, 1959, pp. 54–55.

OECD-Screening-Test (EEC Directive 79/831, Annex V, Part C, 5.2, May 12, 1981.

Zahn, R. and Wellens, H., *Chemiker Zeitung*, vol. 98, 1974, pp. 228–252.

*Primary Examiner*—Paul Lieberman
*Assistant Examiner*—A. Hertzog
*Attorney, Agent, or Firm*—Ernest G. Szoke; Wayne C. Jaeschke; Henry E. Millson, Jr.

[57] ABSTRACT

3-Hydroxy-2,2'-iminodisuccinic acid, water soluble salts thereof, a process for their preparation, and their use as biodegradable complexing agents in detergents.

13 Claims, No Drawings

DERIVATIVE OF AMINOSUCCINIC ACID AS A COMPLEXING AGENT

This invention relates to 3-hydroxy-2,2'-iminodisuccinic acid and soluble salts thereof, to a process for their production and to their use as complexing agents in detergents.

In addition to the obvious need for a high complexing capacity, complexing agents intended for use in modern detergents are increasingly having to satisfy requirements relating to ecologically safe behavior.

DE-OS 22 41 134 describes N-substituted aminohydroxysuccinic acid derivatives which have a more or less high complexing capacity, particularly for alkaline earth metal ions, according to the type and number of substituents bearing carboxyl groups at the N atom. Compounds such as these, which are distinguished by high complexing capacity, show relatively poor degradability whereas more readily degradable products have a comparatively poor complexing capacity.

Accordingly, there is still a need to develop a readily biodegradable and powerful complexing agent.

It has now surprisingly been found that 3-hydroxy-2,2'-iminodisuccinic acid and soluble salts thereof show both a high complexing capacity for the alkali metal ions responsible for the hardness of water and for heavy metal ions and also ready biodegradability and exhibit unexpectedly superior properties through this combination of complexing capacity and biodegradability.

In the context of the invention, soluble substances are understood to be compounds which dissolve in water at 20° C. in a quantity of more than 0.1 gram per liter.

The soluble salts of 3-hydroxy-2,2'-iminodisuccinic acid are preferably those which contain cations from the group of ammonium and alkali metal ions as cations, the ammonium ions preferably being those having the general structural formula $R^1R^2R^3R^4N^+$, in which $R^1$, $R^2$, $R^3$ and $R^4$ independently of one another represent hydrogen, $C_{1-12}$ alkyl radicals or hydroxysubstituted $C_{2-3}$ alkyl radicals. One, two, three or all four carboxylic acid groups of the 3-hydroxy-2,2'-iminodisuccinic acid may be present in the salt form. Accordingly, the compounds in question are compounds corresponding to general formula (I)

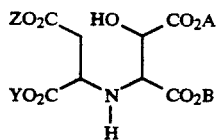

in which A, B, Y and Z independently of one another represent a cation, preferably from the group consisting of hydrogen, ammonium and alkali metal ions, the ammonium ions belonging to those having the general structural formula $R^1R^2R^3R^4N^+$ in which $R^1$, $R^2$, $R^3$ and $R^4$ independently of one another represent hydrogen, $C_{1-12}$ alkyl radicals or hydroxy-substituted $C_{2-3}$ alkyl radicals.

By comparison with the compounds according to DE-OS 22 41 134, it has been found that the 3-hydroxy-2,2'-iminodisuccinic acid according to the invention shows better biodegradability and a higher complexing capacity, particularly at relatively high temperatures, for example 70° to 98° C. (Table 1, Table 2).

The 3-hydroxy-2,2'-iminodisuccinic acid or salts thereof corresponding to formula (I) are prepared by reaction of aspartic acid with epoxysuccinic acid, preferably in molar ratios of 1.05:1 to 1:1.05. The reaction is preferably carried out in aqueous or at least predominantly aqueous medium, the residual solvent consisting of organic compounds inert under the reaction conditions, more particularly methanol, ethanol and/or dioxane. The reaction is preferably carried out under substantially neutral to mildly basic conditions, i.e. in the presence of alkalis, preferably in the form of aqueous solutions of alkali metal or ammonium hydroxides, so that the acid groups of the reactants are present at least partly and preferably completely in the form of carboxylate anions, preferably as alkali metal or ammonium carboxylates. The ammonium hydroxide is preferably selected from compounds corresponding to the general formula $R^1R^2R^3R^4N^+OH^-$, in which $R^1$, $R^2$, $R^3$ and $R^4$ independently of one another represent hydrogen, $C_{1-12}$ alkyl radicals or hydroxysubstituted $C_{2-3}$ alkyl radicals. These hydroxides include, for example, ammonium hydroxide, methyl ammonium hydroxide, ethyl ammonium hydroxide, triethyl ammonium hydroxide, tributyl ammonium hydroxide, didecyl methyl ammonium hydroxide, didecyl dimethyl ammonium hydroxide, diethanolammonium hydroxide and triethanolammonium hydroxide.

In one particularly preferred embodiment of the production process, aspartic acid is initially introduced into water in such a quantity that a 20% by weight to 30% by weight solution or suspension is formed and approximately 2 mol equivalents of an alkali metal hydroxide, preferably sodium hydroxide, and then approximately 1 mol equivalent epoxysuccinic acid dialkali metal salt, preferably disodium salt, are added to the resulting solution or suspension. The mixture is then stirred, preferably until the reactants have completely reacted, which generally takes about 1 to 8 hours. To accelerate the reaction, elevated temperatures, for example in the range from 80° to 100° C., may be applied. After removal of the solvent, for example in a rotary evaporator, the tetraalkali metal salt of 3-hydroxy-2,2'-iminodisuccinic acid is obtained as a more or less colorless solid in a substantially quantitative yield. The 3-hydroxy-2,2'-iminodisuccinic acid can be released from this solid or from the solvent-containing crude product in known manner by addition of typical acids, for example hydrochloric acid or sulfuric acid. The acidification step may be omitted if the salt is to be subsequently used as such. The solvent removal step can be omitted if the product is to be incorporated in liquid formulations or intermediates, for example in pastes or slurries.

In the context of the invention, "epoxysuccinic acid" is used as a synonym both for cis- and for trans-epoxysuccinic acid and for mixtures thereof; the trans form may be present as one of the enantiomers or as a mixture of both, for example as racemate. Similarly, "aspartic acid" stands both for the L- and for D-aspartic acid and also for mixtures thereof, for example the racemate. Accordingly, "3-hydroxy-2,2'-iminodisuccinic acid" stands for all optical isomers having the constitution expressed by this name and for mixtures of such isomers.

Irrespective of the foregoing definition, "aspartic acid" in the context of the invention is preferably naturally occurring L-aspartic acid.

The cis- or trans-epoxysuccinic acid or salts thereof used as educt may be prepared from maleic acid or fumaric acid, for example by the method described by G.B. Payne and P.H. Williams in J. Org. Chem. 24 (1959), 54.

The 3-hydroxy-2,2'-iminodisuccinic acid according to the invention and soluble salts thereof are preferably used as complexing agents in detergents. The complexing agent according to the invention is present in detergents in quantities of 0.01 to 20% by weight and preferably in quantities of 0.1 to 5% by weight. The detergents may be present as solids, for example in powder or tablet form, or in the form of more or less viscous liquids, for example in the form of solutions, suspensions or pastes.

In addition, detergents in which the compounds according to the invention are present may contain any of the components typically present in detergents, more particularly washing-active surfactants, builders, bleaches, inorganic neutral salts, solvents, redeposition inhibitors, enzymes, bleach activators, foam inhibitors, antimicrobial agents and abrasives and also dyes and fragrances.

Where they are present in solid form, the detergents may be produced in known manner, for example by spray drying or granulation. Ingredients which are not stable under such conditions may be subsequently added. Liquid formulations are preferably produced simply by mixing the constituents which may be present either as such or in the form of solutions.

Suitable builders include polycarboxylic acids, more particularly polyacrylic acids, polymethacrylic acids, polymaleic acids and copolymers thereof, layer silicates, more particularly bentonites, and alumosilicates, more particularly zeolites. The acids mentioned above are normally used in the form of their alkali metal salts, more particularly their sodium or potassium salts. The zeolites preferably incorporated in the detergents are particularly zeolites of the NaA or NaX type or mixtures thereof. The detergents according to the invention preferably contain zeolite builders in quantities of 5 to 50% by weight and, more particularly, in quantities of 15 to 40% by weight, optionally in combination with polymer polycarboxylic acids which are preferably present in the detergents according to the invention in quantities of up to 30% by weight and, more particularly, 1 to 20% by weight.

In addition to the water-softening effect, the use of the complexing agents according to the invention in the detergents according to the invention has the advantage that any constituents present which are sensitive to heavy metal ions, including in particular optical brighteners, enzymes and bleaches releasing active oxygen, are very effectively protected against decomposition catalyzed by heavy metal ions.

EXAMPLES

Example 1

8.0 g (0.2 mol) sodium hydroxide and then 17.6 g (0.1 mol) cis-epoxysuccinic acid disodium salt were added with stirring at room temperature to 13.3 g (0.1 mol) L-aspartic acid in 50 ml water. The clear, pale yellow solution was heated under reflux for 8 hours. The solvent was then removed in a rotary evaporator (vacuum). 3-Hydroxy-2,2'-iminodisuccinic acid tetrasodium salt (B1) in the form of a C(3) epimer mixture was obtained in a yield of 36.8 g. According to $^1$H-NMR, the colorless solid contained approx. 5% by weight disodium tartrate (signal at=4.40).

IR (KBr): (cm$^{-1}$)=3400 (O—H); 1590 (C=O carboxylic acid); 1390.

$^1$H-NMR (250 MHz, D$_2$O) : (ppm)=2.45 (m,2H-C(3')); 3.35 (m, H-C(2')); 3.45 and 3.50 (d and d, H-C(2)); 4.15 and 4.20 (d and d, H-C(3)).

The corresponding disodium dipotassium salt was analogously prepared by reaction of aspartic acid neutralized with potassium hydroxide with cis-epoxysuccinic acid disodium salt.

The concentrated solutions obtained in the synthesis described above, which have an active substance content of more than 40%, may also be directly used without rotary evaporation and isolation of the reaction product.

Example 2: Degradability Test

The aquatic biodegradability of the products listed in Table 1 was tested by the modified OECD Screening Test (EEC Directive 79/831, Annex V, Part C, 5.2). The results are expressed as the percentage reduction in the DOC value (dissolved organic carbon) after 28 days under aerobic degradation conditions after acclimatization of the bacteria by the Zahn-Wellens method (R. Zahn, H. Wellens, Chem. Ztg. 98 (1974) 228).

TABLE 1

| Biological degradability | |
|---|---|
| Reaction product of epoxydisuccinic acid disodium salt with the sodium salt of | Degradability [%] |
| a) L-aspartic acid (B1) | 80–89 |
| b) Glutamic acid | 51–57 |
| c) Ethylenediamine | 7–10 |
| d) Alanine | 12–14 |

The product according to the invention (line a) degrades relatively easily compared with the similar compounds of lines b to d.

Example 3: Tests for Complexing Capacity

Solutions of approx. 1 g of the substances listed in Table 2 in approx. 250 ml distilled water were adjusted to pH 11 by addition of 2 N NaOH, 10 ml 2% by weight sodium carbonate solution were added and the clear solutions obtained at the temperatures listed in Table 2 were titrated with 0.25 N calcium chloride solution until the first signs of clouding appeared (photometric determination, measuring wavelength 400 nm). The complexing capacity of B1 for iron was analogously determined by titration with aqueous FeCl$_3$ solution and was found to be 1139 mg Fe$^{3+}$ per g complexing agent at 20° C. and 289 mg Fe$^{3+}$ per g complexing agent at 98° C.

TABLE 2

| | Complexing capacity | |
|---|---|---|
| Reaction product of epoxysuccinic acid disodium salt with the sodium salt of | mg CaCO$_3$ per g complexing agent | |
| | 20° C. | 70° C. |
| a) L-aspartic acid (B1) | 320 | 280 |
| b) Glutamic acid | 310 | 200 |
| c) Ethylenediamine | 290 | 250 |
| d) Alanine | 300 | 240 |

By comparing the results of ligand and ligand+metal titrations, compound B1 was found to have a Cu complexation constant of 6.4. Its Ca complexation constant was also measured. The Ca complexation constants typical complexing agents determined by the same method are shown for comparison.

TABLE 3

| Compound | Complexation constants pK$_{Ca}$ |
|---|---|
| 3-Hydroxy-2,2'-iminodisuccinic acid (B1) | 5.8 |
| Hydroxyethyl-2,2'-iminodiacetic acid | 4.6 |
| Isoserine-N,N-diacetic acid | 5.6 |

Example 4

Using a commercially available boil-wash detergent powder, 3.5 kg clean ballast washing were washed in a drum-type washing machine (Miele W 760), one-wash cycle (wash program 241/22), with 2.1 g fabric samples stained with a bleachable soil (red wine on cotton; red currant on cotton; tea on cotton, red wine on crease-resistant cotton; tea on crease-resistant cotton; red wine on crease-resistant cotton/polyester; tea on crease-resistant cotton/polyester) at 90° C. with water having a hardness of 16° dH (160 mg CaO/liter) to which 5 ppm Cu(II) had been added. A commercially available boil-wash detergent powder (W1), to which 0.25% by weight of complexing agent B1(W2) and 0.25% by weight diethylenetriamine penta-(methylenephosphonic acid) pentasodium salt (DETMP) (W3) had been added, was used. The detergents W1, W2 and W3 were added in quantities of 140 g per wash load. Four washes were carried out. The average remission value of the washed test swatches for the seven test soils mentioned Was 69.2 where detergent W2 according to the invention was used. The corresponding value for detergent W1 free from complexing agent was significantly worse (67.0) while the use of the phosphonate-containing detergent W3 did not produce a significantly better result than the use of W2.

The washing results show that compound B1 according to the invention suppresses perborate decomposition by heavy metals at least as well as a known effective complexing agent from the class of phosphonates.

We claim:
1. 3-Hydroxy-2,2'-iminodisuccinic acid and water soluble salts thereof.
2. A water soluble salt of claim 1 corresponding to formula (I)

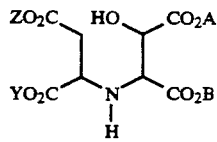

in which A, B, Y and Z independently of one another represent a cation selected from the group consisting of hydrogen, ammonium and alkali metal ions, the ammonion ions belonging to those having the formula $R^1R^2R^3R^4N^+$, in which $R^1$, $R^2$, $R^3$ and $R^4$ independently of one another represent hydrogen, $C_{1-12}$ alkyl radicals or hydroxysubstituted $C_{2-3}$ alkyl radicals.

3. The water soluble salt of claim 2 wherein the cation A is an alkali metal ion and A, B, Y and Z are the same.

4. A process for the preparation of 3-hydroxy-2,2'-iminosuccinic acid or a salt thereof comprising the steps of reacting together
A) epoxysuccinic acid or a monosalt or disalt thereof, and
B) aspartic acid or a monosalt or disalt thereof.

5. The process of claim 4 wherein the molar ratio of epoxysuccinic acid or epoxysuccinic acid salt to aspartic acid or aspartic acid salt is in the range from about 1.05:1 to about 1:1.05.

6. The process of claim 4 wherein a monoammonium or diammonium salt or alkali metal salt of aspartic acid is reacted with a monoammonium or diammonium salt or alkali metal salt of epoxysuccinic acid, the ammonium ions being selected from those corresponding to the formula $R^1R^2R^3R^4N^+$, in which $R^1$, $R^2$, $R^3$ and $R^4$ independently of one another represent hydrogen, $C_{1-12}$ radicals or hydroxy substituted $C_{2-3}$ alkyl radicals.

7. The process of claim 4 wherein epoxysuccinic acid is initially introduced in the form of an about 20% by weight to an about 30% by weight solution or suspension in water, said solution or suspension being optionally neutralized completely or partly by addition of a solution of ammonium hydroxide or alkali metal hydroxide; the aspartic acid component, which can optionally be neutralized completely or partly by a solution of ammonium or alkali metal hydroxide, is added to the above solution or suspension, wherein the ammonium hydroxide is selected from compounds corresponding to the formula $R^1R^2R^3R^4N^+OH$, in which $R^1$, $R^2$, $R^3$ and $R^4$ independently of one another represent hydrogen, $C_{1-12}$ alkyl radicals or hydroxy substituted $C_{2-3}$ alkyl radicals, and the reaction mixture is kept at a temperature of from about room temperature to about 100° C. for from about 0.05 to about 8 hours.

8. In a detergent composition for cleaning an/or disinfecting solid surfaces or textiles, the improvement comprising the presence therein of from about 0.01 to about 20% by weight of at least one complexing agent selected from the group consisting of 3-hydroxy-2,2'-iminodisuccinic acid and water soluble salts thereof.

9. The detergent composition of claim 8 wherein the composition contains from about 0.1 to about 5% by weight of the complexing agent.

10. The detergent composition of claim 8 wherein the composition also contains from about 5 to about 50% by weight of a zeolite.

11. The detergent composition of claim 10 wherein the composition contains from about 15 to about 40% by weight of a zeolite.

12. The detergent composition of claim 10 wherein the composition also contains up to about 30% by weight of a polymer polycarboxylic acid.

13. The detergent composition of claim 11 wherein the composition also contains from about 1 to about 20% by weight of a polymer polycarboxylic acid.

* * * * *